(12) United States Patent
Dow et al.

(10) Patent No.: US 10,540,994 B2
(45) Date of Patent: *Jan. 21, 2020

(54) PERSONAL DEVICE FOR HEARING DEGRADATION MONITORING

(71) Applicant: International Business Machines Corporation, Armonk, NY (US)

(72) Inventors: Eli M. Dow, Wappingers Falls, NY (US); Thomas D. Fitzsimmons, Lancaster, PA (US); Maurice M. Materise, Poughkeepsie, NY (US); Jessie Yu, Wappingers Falls, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/384,162

(22) Filed: Apr. 15, 2019

(65) Prior Publication Data

US 2019/0244631 A1    Aug. 8, 2019

Related U.S. Application Data

(63) Continuation of application No. 15/292,164, filed on Oct. 13, 2016.

(51) Int. Cl.
*G10L 25/66* (2013.01)
*G06F 17/27* (2006.01)
(Continued)

(52) U.S. Cl.
CPC ............ *G10L 25/66* (2013.01); *A61B 5/0002* (2013.01); *G06F 17/279* (2013.01);
(Continued)

(58) Field of Classification Search
CPC ...................................................... H04R 25/30
(Continued)

(56) References Cited

U.S. PATENT DOCUMENTS 6,674,862 B1    1/2004  Magilen
7,680,645 B2 *  3/2010  Li .......................... G06F 11/28
                                                  703/22
(Continued)

OTHER PUBLICATIONS

Clason; "The Best Apps for Phone Captioning"; Healthy Hearing; Mar. 27, 2015; 5 pages.
(Continued)

*Primary Examiner* — Michael N Opsasnick
(74) *Attorney, Agent, or Firm* — Cantor Colburn LLP; Teddi Maranzano

(57) ABSTRACT

Aspects relate to computer implemented methods and systems for monitoring a user's hearing and comprehension. The methods and systems include receiving, by an audio capture device, a first audio input, receiving, by the audio capture device, a second audio input, converting the first and second audio inputs into respective first and second audio signals, transcribing the first and second audio signals into respective first and second transcriptions, analyzing, by a processor of the remote resource, the first and second transcriptions to determine if a content of the second transcription is related to a content of the first transcription to determine degradation of hearing of the user.

20 Claims, 3 Drawing Sheets

(51) Int. Cl.
*A61B 5/00* (2006.01)
*H04R 25/00* (2006.01)
*G10L 15/26* (2006.01)
*G10L 17/04* (2013.01)
*G10L 25/90* (2013.01)

(52) U.S. Cl.
CPC ............ H04R 25/505 (2013.01); *G10L 15/26* (2013.01); *G10L 17/04* (2013.01); *G10L 25/90* (2013.01); *H04R 25/554* (2013.01); *H04R 25/70* (2013.01)

(58) Field of Classification Search
USPC .......................................... 381/314; 600/300
See application file for complete search history.

(56) References Cited

U.S. PATENT DOCUMENTS

| | | | | |
|---|---|---|---|---|
| 8,010,366 | B1* | 8/2011 | Kearby | G09B 21/006 704/271 |
| 9,336,689 | B2 | 5/2016 | Romriell et al. | |
| 2002/0069069 | A1 | 6/2002 | Kanevsky et al. | |
| 2006/0029912 | A1* | 2/2006 | Kearby | G09B 5/04 434/116 |
| 2008/0281620 | A1 | 11/2008 | Schalk et al. | |
| 2009/0074216 | A1 | 3/2009 | Bradford et al. | |
| 2011/0125063 | A1* | 5/2011 | Shalon | A61B 5/0006 600/590 |
| 2011/0256513 | A1 | 10/2011 | Levitt et al. | |
| 2012/0059651 | A1 | 3/2012 | Delgado et al. | |
| 2012/0173281 | A1* | 7/2012 | DiLella | G06Q 10/00 705/3 |
| 2013/0144619 | A1* | 6/2013 | Lord | G06F 3/165 704/235 |
| 2013/0308763 | A1* | 11/2013 | Engelke | H04M 11/066 379/52 |
| 2013/0343584 | A1 | 12/2013 | Bennett et al. | |
| 2013/0346332 | A1 | 12/2013 | Schalk et al. | |
| 2014/0196133 | A1* | 7/2014 | Shuster | H04L 63/126 726/7 |
| 2014/0314261 | A1* | 10/2014 | Selig | H04R 25/50 381/314 |
| 2015/0036853 | A1 | 2/2015 | Solum et al. | |
| 2015/0149169 | A1 | 5/2015 | Chang | |
| 2015/0180856 | A1* | 6/2015 | Shuster | H04L 63/126 726/7 |
| 2015/0189086 | A1 | 7/2015 | Romano et al. | |
| 2015/0199977 | A1* | 7/2015 | Ungstrup | H04R 25/55 704/260 |
| 2015/0287408 | A1* | 10/2015 | Svendsen | G10L 15/26 704/235 |
| 2015/0289062 | A1* | 10/2015 | Ungstrup | H04R 25/554 381/314 |
| 2015/0341734 | A1 | 11/2015 | Sherman | |
| 2016/0071526 | A1* | 3/2016 | Wingate | G10L 21/028 704/233 |
| 2016/0080876 | A1 | 3/2016 | Lunner | |
| 2016/0111111 | A1* | 4/2016 | Levitt | G10L 21/02 704/231 |
| 2016/0157030 | A1 | 6/2016 | Odame et al. | |
| 2016/0234606 | A1* | 8/2016 | Selig | H04R 25/50 |
| 2016/0275942 | A1* | 9/2016 | Drewes | G06F 17/2735 |
| 2017/0206914 | A1 | 7/2017 | Engelke et al. | |

OTHER PUBLICATIONS

Medwetsky; "Mobile Device Apps for People with Hearing Loss, Expanding the Horizons of Hearing Access"; Hearing Loss Magazine; Nov.-Dec. 2015; 7 pages.
Tanasychuk, et al.; "How to Connect Hearing Aids and Use Audio Accesibility on iPhone and iPad"; May 18, 2016; 12 pages.
List of IBM Patents or Patent Applications Treated as Related; Appendix P Filed Apr. 15, 2019; 2 Pages.

* cited by examiner

US 10,540,994 B2

PERSONAL DEVICE FOR HEARING DEGRADATION MONITORING

CROSS REFERENCE TO RELATED APPLICATIONS

This application is a Continuation Application of U.S. Non-Provisional application Ser. No. 15/292,164, filed Oct. 13, 2016, which is incorporated herein by reference in its entirety.

BACKGROUND

The present disclosure relates generally to audio and hearing aid devices and, more specifically, to devices and systems for monitoring hearing loss and/or comprehension of users.

The wearable hearing aid device is traditionally based on a customized hardware device that the hearing impaired persons wear around or in their ears. Because hearing loss is highly personal, traditional hearing aid devices can require special adjustment (or "tuning") from time to time or may be based on a single medical diagnosis or may be calibrated on a specific testing event. However, resetting or tuning of the hearing aid can be time consuming and expensive, and proper adjustment may be difficult. Additionally, people who have hearing loss may not know how severe their loss is, or how it progresses over time. Thus, a user of the hearing aid may not know that the tuning should be performed.

SUMMARY

According to embodiments, methods, systems, and computer program products are provided for monitoring a user's hearing and comprehension. The methods and systems include receiving, by an audio capture device, a first audio input and a second audio input. The first and second audio inputs are converted into respective first and second audio signals and transmitted to a remote resource. The first and second audio signals are transcribed into respective first and second transcriptions and analyzed by a processor of the remote resource. The analysis is made to determine if a content of the second transcription is related to a content of the first transcription. The analysis is recorded to track a hearing and comprehension ability of the user.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Embodiments described herein are directed to systems and methods for monitoring and detecting a user's hearing ability and/or comprehension of spoken conversation. The systems and methods include an audio capture device, such as a hearing aid, that is in communication with a connected remote resource, such as a smartphone or smartwatch. The systems and methods are configured to enable autonomous (e.g., no user interaction) tracking and detection of possible hearing loss, mental deterioration, and/or mechanical/electrical issues related to a hearing aid.

Figure 1:
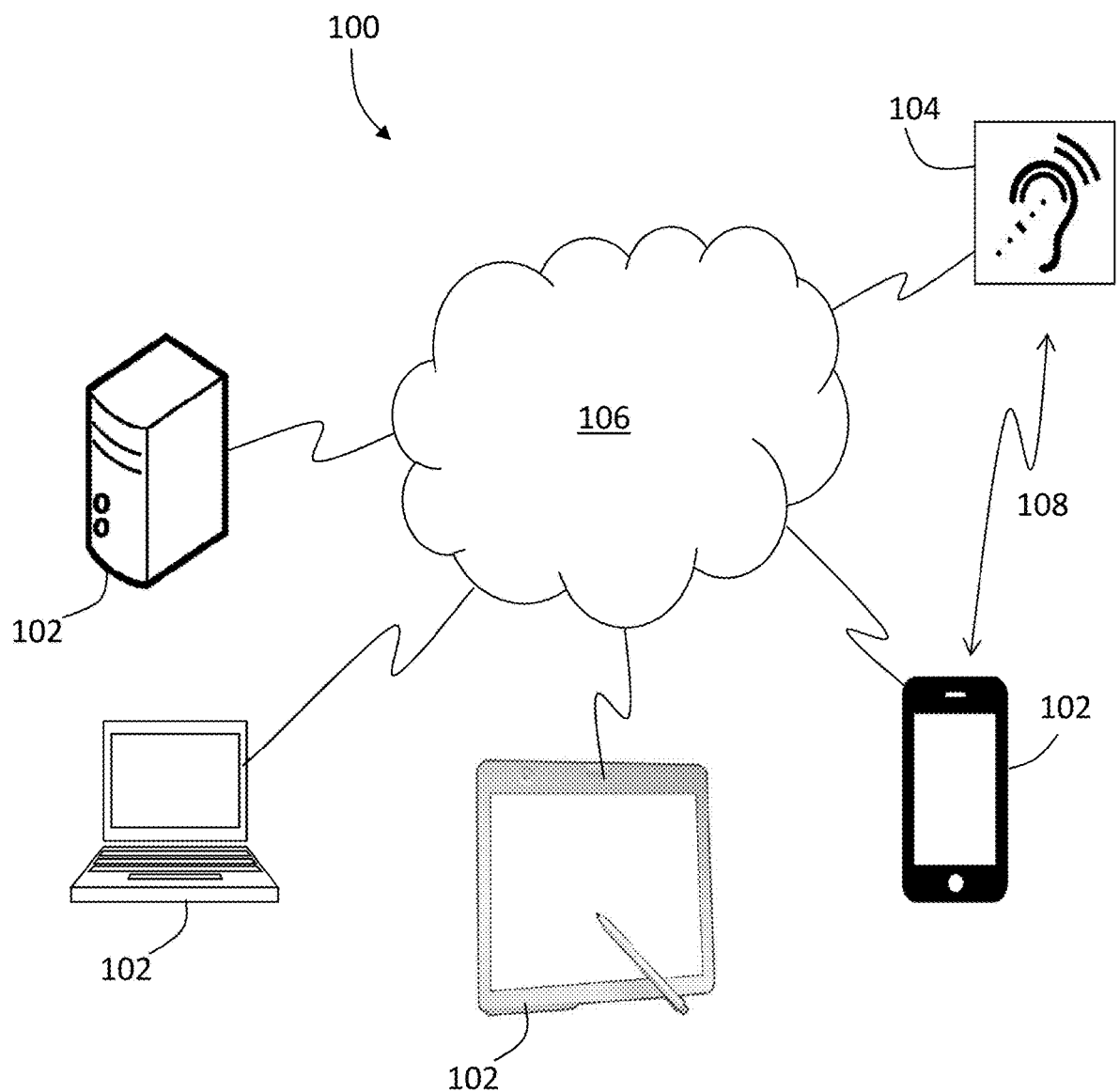
FIG. 1 depicts a block diagram of a system for enabling hearing aid and monitoring functionality in accordance with an embodiment of the present disclosure.

Referring to FIG. 1, a block diagram of a system 100 for using a hearing degradation monitoring system pertaining to a discussion in accordance with a non-limiting embodiment of the present disclosure is shown. The system 100 includes a hearing aid 104 for performing audio capture and amplification to enable a user to hear audio in proximity to the user. For example, the hearing aid 104 can be a hearing aid, microphone/speaker device, headphones, or other electronic devices that can be inserted into a user's ear or otherwise installed and/or configured with a user, including but not limited to implanted hearing aids. The hearing aid 104 can be in communication with a remote resource 102 such as a smart phone, personal tablet, laptop computer, or other personal electronic device that includes software and hardware and/or data processing and transmitting software and hardware to enable embodiments described herein.

For example, the hearing aid 104 and/or a paired or otherwise connected remote resource 102 can be configured to execute one or more computer programs located on the hearing aid 104 and/or located on one or more remote resources 102 through communication therewith. As shown, the system 100 may incorporate one or more remote resources 102, such as a laptop, a smartphone, smartwatch, a tablet, and/or a remote server or storage device (e.g., cloud-based storage) although other remote resources such as personal electronic devices or internet based sources may be used with systems and processes described herein.

As noted, the system 100 depicted in FIG. 1 includes one or more remote resources 102 that can be operably connected and/or in communication with the hearing aid 104 to initiate, interact with, and/or receive information therefrom. In some embodiments, the remote resources 102 can automatically access the hearing aid 104 during processing and operation as described herein. As shown, the remote resources 102 are coupled to the hearing aid 104 via a network 106. Some of the remote resources 102 may be implemented using general-purpose computers executing computer programs for carrying out various processes and/or programs. The devices of the remote resources 102 may be user devices such as personal computers (e.g., laptops, tablet computers, cellular telephones, etc.). In some embodiments, such as if the remote resources 102 are personal computers or smartphones, the processing described herein may be shared by one or more remote resources 102. The remote resources 102 may also include game consoles, network management devices, field programmable gate arrays, etc.

The network 106 may be any type of known network including, but not limited to, a wide area network (WAN), a local area network (LAN), a global network (e.g. Internet), a virtual private network (VPN), a cloud network, and an intranet. The network 106 may be implemented using a wireless network or any kind of physical network implementation known in the art. A remote resource 102 may be coupled to the hearing aid 104 through multiple networks 106 (e.g., cellular and Internet) so that not all remote resources 102 are coupled to the hearing aid 104 through the same aspect of network 106. One or more of the remote resources 102 and the hearing aid 104 may be connected to the network 106 in a wireless fashion. In one non-limiting embodiment, the network is the Internet and one or more remote resources 102 execute a user interface application (e.g. a web browser or app) to communicate to each other through the network 106.

In another non-limiting example embodiment, one or more remote resources 102 may be connected directly (i.e., not through the network 106) to the hearing aid 104. That is, as shown, a direct or dedicated communication link 108 may be formed between the hearing aid 104 and a remote resource 102 (e.g., a smartphone, smartwatch). Such connection may be made by Bluetooth® connection or other near-field communication protocol.

In some embodiments, the hearing aid 104 and/or one or more connected remote resources 102 may be configured to access one or more programs, applications, and/or software that are accessible in the cloud, e.g., stored on one or more internet based servers. As such, a storage device or remote server may be implemented as one of the remote resources 102 using a variety of devices for storing electronic information. In an example embodiment, data stored in the storage device or remote server may include, but is not limited to, one or more user applications and/or data, including but not limited to, historical audio data, learned responses, user-specific data, metadata related to the same, etc., and other data utilized by embodiments described herein. It is understood that the remote server or storage device may be implemented using memory contained on a remote resource 102 or that it may be a separate physical device, e.g., an internet server with cloud storage. The storage device remote resource 102 may be logically addressable as a consolidated data source across a distributed environment that includes the network 106. Information stored in the storage device may be retrieved and manipulated via another remote resource 102, e.g., a laptop, smartphone, smartwatch. The hearing aid 104 may be provided with a processor or controller, memory, and various other electronic components configured to enable audio capture, feedback actions, processing, amplification, etc. to enable a user to be provided with aided hearing.

The hearing aid 104 and/or one or more remote resources 102, in some embodiments, may execute one or more computer programs, e.g., an audio capture and monitoring application, to provide aspects of embodiments as described herein. Processing may be shared by the hearing aid 104 and one or more of the remote resources 102. As previously described, it is understood that separate servers may be utilized to implement network server functions and application server functions. Alternatively, a network server, a firewall, and an application server may be implemented by a single server executing computer programs to perform the requisite functions.

In accordance with embodiments described herein, a user may use a hearing aid 104 to enable improved or aided hearing, such as audio amplification of conversations the user is having with other persons. Further, in some embodiments, the hearing aid 104 and a paired or connected remote resource 102 can form a hearing and audio monitoring system. That is, in some embodiments, the combination of the hearing aid 104 and a remote resource 102 can form a hearing aid and monitoring system that can provide improved functionality and monitoring features to users that may be hard of hearing.

In some embodiments, the remote resource 102 can include one or more microphones or other audio recording or capturing devices and/or functionality. Such audio recording may be independent from the audio capture and processing performed by the hearing aid 104. In other embodiments, the remote resource 102 can be provided with audio data captured by the hearing aid 104. Further still, a combination of audio capture on the remote resource 102 and audio data obtained at the hearing aid 104 can be used in accordance with embodiments of the present disclosure.

In a non-limiting example, when audio is received at the hearing aid 104, the hearing aid 104 can be configured to transmit audio data to a paired remote resource 102 (e.g., a smartphone or smartwatch). That is, the hearing aid 104 can relay data or an audio signal through a Bluetooth® connection with the remote resource 102. The connected remote resource 102 can be used to enable transcription of the audio signal or audio data which can be a conversation the user of the hearing aid 104 is participating in. Accordingly, a user that is hard of hearing can have a written or visual record or presentation of what is being said to the user.

Further, in accordance with various embodiments of the present disclosure, a data collection, and monitoring aspect can be incorporated into the hearing aid and monitoring system. For example, the hearing aid and monitoring system can learn from recorded audio signals to monitor and identify hearing-related conditions of the user of the system. For example, as described herein, the hearing aid and monitoring system can be configured to learn the voice of a user of the system and thus can track when the user speaks. Further, the hearing aid and monitoring system can be configured to identify when questions or other statements are presented to the user audibly. From this, the hearing aid and monitoring system can perform an analysis or comparison between non-user audio input (e.g., a question) and a user response (e.g., answer to question).

As noted, by setting the hearing aid 104 to relay a received signal through a Bluetooth® transmitter to a paired smartphone or other remote resource 102, many applications become available such as transcribing the user's conversations recorded or detected by the hearing aid and monitoring system. In the simplest case, the hearing aid and monitoring system can provide hard-of-hearing users a way of seeing what was said to them on their phone or smartwatch rather than requiring someone speaking to that user to repeat themselves or shout in extreme cases of hearing loss. Secondly, embodiments of the present disclosure can include a hearing aid and monitoring system with analytics that can be layered or applied on top of the conversations held (e.g., recorded audio signals) to determine if the hearing aid wearer (e.g., user) is correctly interpreting the signals received by the hearing aid itself. For example, embodiments provided herein can enable a determination if the user is receiving a clear signal in the hearing aid, but mishearing the conversation, which can cause confusing exchanges with another participant leading to frustration or misunderstanding. Furthermore, by applying analytics on the audio characteristics (e.g., frequency) of misheard or likely misidentified conversations over time, that hearing aid and monitoring system can generate data and historical tracking related to hearing loss progression. For example, if the frequency of mishearing or statistically inappropriate responses or clarifying responses occurs more frequently over time there may be some progression or degradation in a user's hearing loss. Alternatively, such information can indicate a need for a repair or calibration of the hearing aid (e.g., battery replacement) or indication of a malfunction in the hearing aid.

In view of the above, embodiments of the present disclosure are directed to, in part, methods for hearing aid assistance and user hearing ability monitoring. A hearing aid is configured to relay a received signal to a connected smartphone or watch (remote resource) using Bluetooth® or other close proximity wireless technology. Such signal relay can enable monitoring and tracking of a user's hearing degradation over time. In accordance with some embodiments, alerts can be provided to a user regarding a hearing aid operating status, such as battery levels or other mechanical/electrical issues related to the hearing aid.

Figure 2:
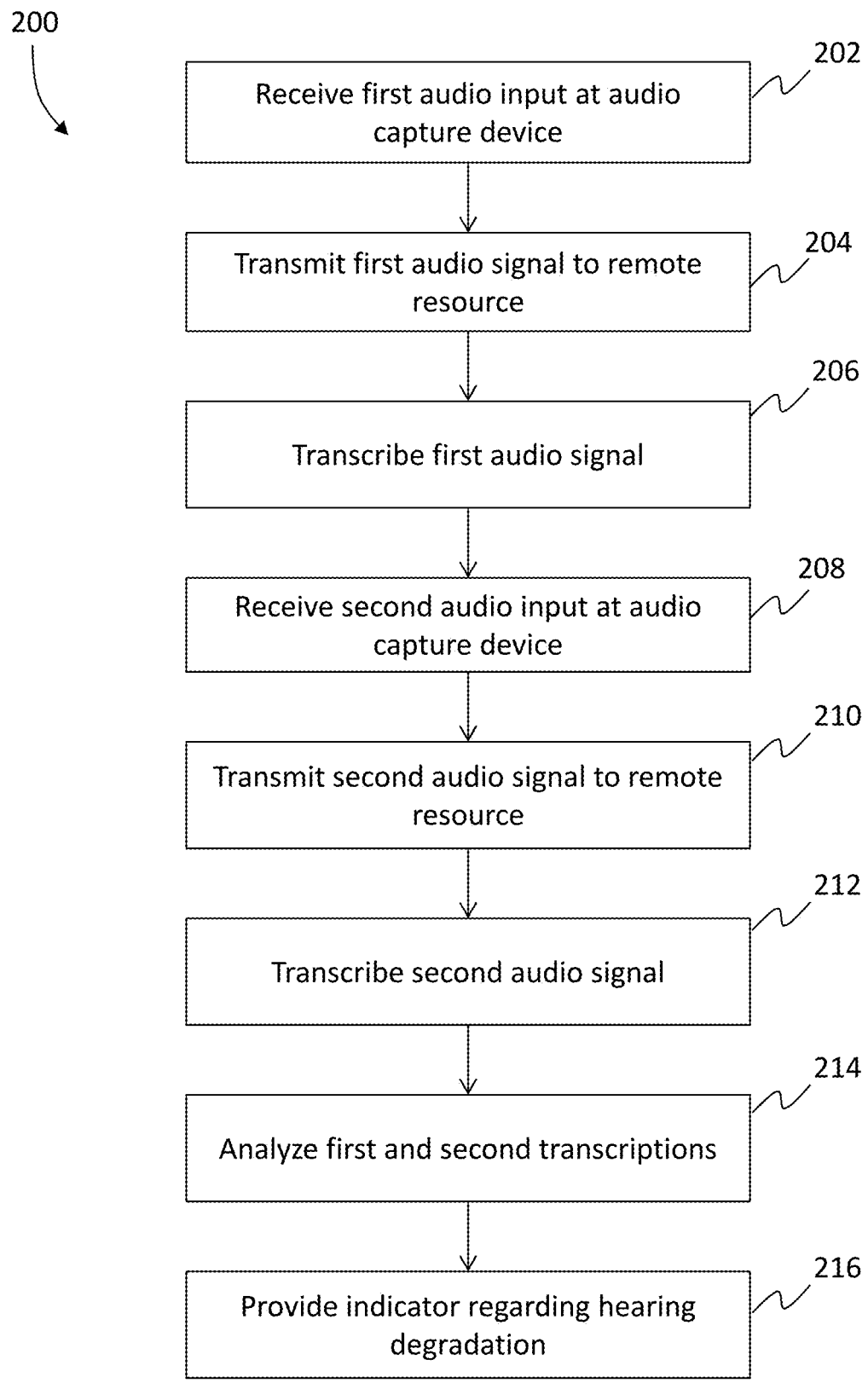
FIG. 2 is a flow process for performing comprehension or hearing ability of a user in accordance with an embodiment of the present disclosure.

For example, turning now to FIG. 2, a flow process 200 in accordance with an embodiment is shown. The flow process 200 is shown in a particular order of steps, however, those of skill in the art will appreciate that the flow process 200 can be performed in various other orders of steps and/or various steps can be performed simultaneously. Further, additional and/or alternative steps or processes can be included within the flow process 200 without departing from the scope of the present disclosure. The flow process 200 can be implemented, for example, by a hearing aid that is used by a user and a connected remote device, such as a smartphone or smartwatch.

At block 202, a first audio input is received at an audio capture device. The audio capture device can be the hearing aid of the user. In other embodiments, the audio capture device can be the remote resource of the user. The audio input that is received by the audio capture device is processed and/or converted to a digital signal at the audio capture device. The first audio input can be a verbal communication from someone other than the user of the hearing aid. For example, the first audio input may be a question or statement posed to the user by another person (e.g., a conversation).

At block 204, when the audio capture device is a hearing aid, the first audio signal is transmitted to the connected remote resource. Such transmission can be by Bluetooth® or other digital transmission and/or communication protocol.

At block 206, the remote resource can transcribe the first audio signal into text. Optionally, the transcription of the first audio signal can be displayed on a screen of the remote device. For example, if the user wishes to read what was said to them, the transcription can be displayed for ease of access and understanding. In some embodiments, the remote resource may not have a display screen or the user may not have easy access to view the screen. However, such display of the transcription is not required in various embodiments of the present disclosure.

At block 208, a second audio input is received at the audio capture device. The second audio input can be a response or reply provided by the user of the audio capture device. In some embodiments, the audio capture device and/or the remote resource can be configured to detect the user's voice (e.g., detected audio characteristics include, but are not limited to, audio frequency, cadence, unvoiced consonants, clicks, whistling, whispering, pitch, tone, etc.). The system can be configured to track or monitor to ensure that the second audio input is related to the first audio input. For example, in some embodiments, a timer can be used to measure a time between an end of the first audio input and a start of the second audio input. The audio capture device can convert the second audio input into a second audio signal (e.g., a digital format of information capturing the audio of the second audio input).

At block 210, the second audio signal is transmitted to the remote resource. At block 212 the second audio signal is transcribed into text format, for possible display and processing.

At block 214, the first and second transcriptions of the first and second audio signals (e.g., the first and second audio inputs) are analyzed. The analysis performed at block 214 is a comparison between the first and second transcriptions. Based on machine learning or other analytical programs and processes, the remote resource can determine if the content of the second transcription makes sense as a follow up to the first transcription. That is, a machine comparison can be performed to determine if the user's response to another person actually makes sense, i.e., does the content of the second audio input semantically match the content of the first audio input. One consideration or parameter may be a timing of the first and second transcriptions. For example, the transcriptions may be analyzed if a recorded time of the first audio input and the second audio input occur within a predefined period of time. Another consideration may be identification within the first transcription of the user's name, but no response is provided by the user. That is, if the user's hearing is insufficient to register that the user is being spoken to, this may be a factor for noting a user's degradation of hearing.

For example, if the first transcription includes key words related to weather (e.g., "weather," "rain," "sunny," etc.) the processing of the remote resource can determine if the second transcription is similarly directed in terms of content. That is, by performing analytics on the first and second transcriptions, the hearing aid and monitoring system in accordance with the present disclosure can determine if a user is properly responding to words posed to them by determining if the second transcription matches the content of the first transcription.

The analytics employed herein can include various language and/or audio processing techniques. For example, various machine learning and analytically techniques can be used, including but not limited to, language detection, relation extraction, concept tagging, emotional analysis, pitch/tone analysis, cadence analysis, etc.

If the second transcription correlates or matches the first transcription, then the hearing aid and monitoring system will determine that the user properly heard the speaker of the first audio input. As used herein, a correlation or match indicates a relationship between the content of the first and second transcriptions or a relationship between the content of the first and second audio inputs/audio signals.

However, if the second transcription does not correlate, match, or otherwise related to the first transcription, a record can be made to indicate a possible degradation of hearing of the user. For example, at block 216, the hearing aid and monitoring system can provide an indicator regarding the hearing degradation. The indicator can be a recording of a data point within memory of the hearing aid and monitoring system (e.g., memory of the remote resource). In other configurations, or in combination therewith, the indicator can include a notification presented on a screen of the remote device, a transmission of such indication to a health care provider, inclusion of such occurrence within a user's medical record, a recorded event in tracking software or application, etc.

Figure 3:
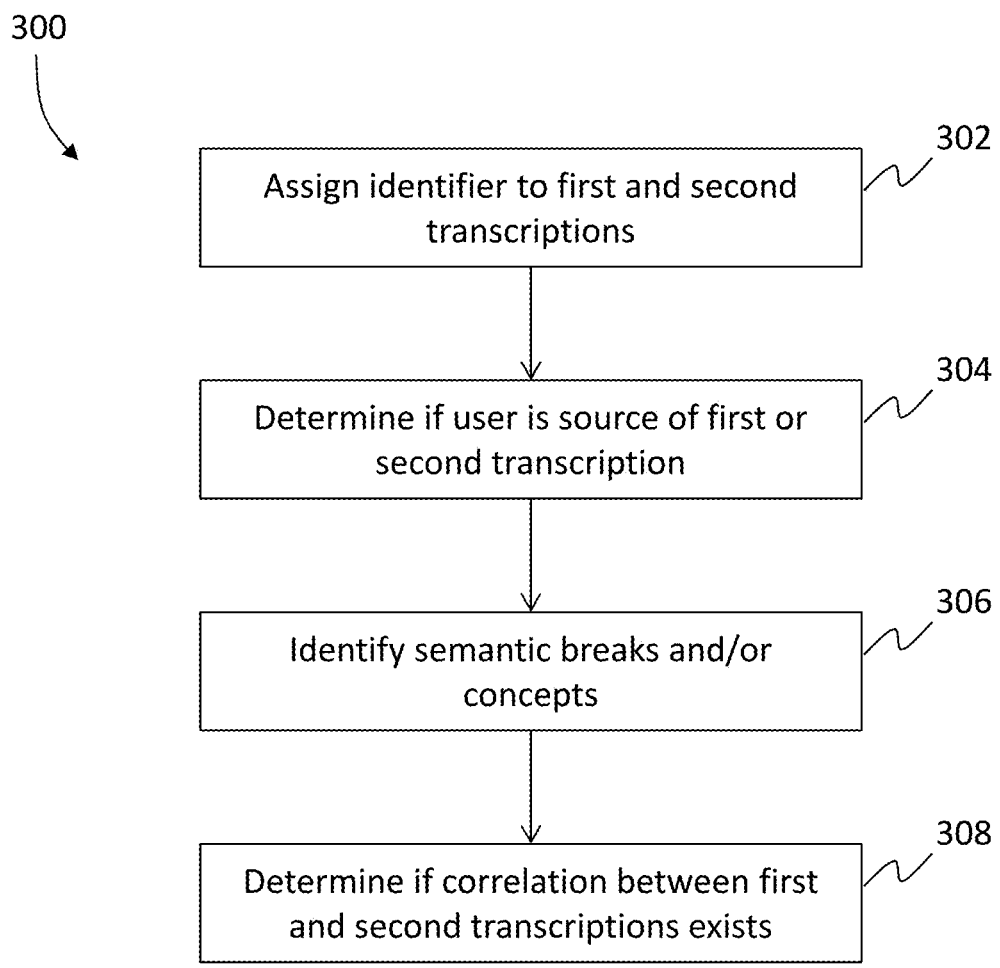
FIG. 3 is a flow process for performing analytics in accordance with an embodiment of the present disclosure.

Turning now to FIG. 3, a flow process 300 for performing analytics in accordance with an embodiment of the present disclosure is shown. The flow process 300 can be a flow process performed during block 214 of flow process 200 shown in FIG. 2.

At block 302, the first and second transcriptions can be assigned an identifier, such as "person1" and "person2" or similar identifying or categorization. For example, a first speaker or source of the content of the first transcription may be a person talking to a user of a system described herein. The process, at block 302, may identify or assign "non-user" status to the first speaker, and thus the first transcription. Such determination may be based on a user profile that is used to determine when the user of the system is speaking and thus the source of the content of a transcription. Similarly, the system may assign "user" status to the second speaker, and thus the second transcription, based on a user profile that is part of the system.

Identification of the source of the transcriptions can be obtained through analysis and/or processing of the audio signal associated with each transcription. For example, the process can be to analyze volume, language usage by the user, pitch, tone, cadence, etc.

At block 304, the system will determine if either transcription derives from speaking by the user. If the user is identified as the source of either of the transcriptions, the flow process 300 will continue. However, if the user is not identified as a source of either transcription, the flow process 300 can end. Accordingly, the system may be configured to eliminate or ignore conversations that the user does not participate in.

At block 306, identification of semantic breaks, concepts within the content of the transcriptions, etc. is performed. For example, the transcriptions can be analyzed for identifying words, identifying phrases, tone, volume, pitch, etc. to determine the content of the transcriptions and the meaning therein.

At block 308, a determination regarding the content of the first and second transcriptions is made. For example, as described above, if the second transcription correlates or matches the first transcription, then the hearing aid and monitoring system will determine that the user properly heard the speaker of the first audio input. As noted, a correlation or match indicates a relationship between the content of the first and second transcriptions or a relationship between the content of the first and second audio inputs/audio signals. If the second transcription does not correlate, match, or otherwise related to the first transcription, a record can be made to indicate a possible degradation of hearing of the user.

Based on the determination at block 308, the system may make a determination regarding the user's hearing ability. For example, after block 308, block 216 of process 200 can be performed.

In some non-limiting embodiments, hearing aid and monitoring systems of the present disclosure can include profile generation and evolution for a particular user. For example, when a user first employs a hearing aid and monitoring system described herein, the system can be calibrated to the user. That is, a user profile can be generated through, for example, machine learning. The user profile can include voice recognition data that includes information related to language usage by the user, speaking, pitch, tone, cadence, etc. The system can actively improve and over time update the user profile through machine learning. Accordingly, hearing aid and monitoring systems of the present disclosure can enable customized profiles to ensure proper identification and tracking of a user's comprehension and/or hearing ability.

Accordingly, embodiments provided herein are directed to a process of comparing or analyzing two input signals related to audio heard by a user of a hearing aid, and determining if the user heard what was actually said (or a misinterpretation was made). To enable such process, and to maximize the effectiveness, various embodiments of the hearing aid and monitoring systems of the present disclosure can perform machine learning related to the user. For example, hearing aid and monitoring systems of the present disclosure can learn to identify the particular user such that received audio can be identified as the user. As such, the hearing aid and monitoring system can also identify when another person is speaking to the user. Accordingly, direct user input can be eliminated. That is, user input and interaction with the hearing aid and monitoring system is not required, but rather the hearing aid and monitoring system can be fully autonomous.

For example, hearing aid and monitoring systems of the present disclosure employ automated inference analytics operating upon the text transcription to automatically determine if the user is hearing what is transcribed (e.g., on screen). Further, advantageous, in addition to being autonomous, embodiments provided herein enable tracking, monitoring, and automatic indication of hearing degradation. For example, in one non-limiting embodiment, a mean number of contextual or cognitive breaks (e.g., incorrect hearing is detected based on first and second inputs) in conversation per day can be recorded with the hearing aid and monitoring system. Then, if the mean number of incorrect hearing events increasing over time, such record can indicate hearing loss or dementia by the user (e.g., hard of hearing or lack of comprehension of first input based on content of second input).

Stated another way, embodiments of the present disclosure are directed to autonomously tracking cognitive breaks in dialog and generating a historical record of such cognitive breaks in order to track potential hearing loss, hearing degradation, and/or loss or degradation of mental faculties of a user. A semantic check can be used to determine, objectively, if the user lacks in comprehension or hearing, and thus an objective monitoring can be performed with embodiments of the present disclosure.

Technical effects and benefits include hearing aid and monitoring systems configured to autonomously record and identify instances of lack of hearing or understanding by a user based on comparison of a first audio input and a second audio input. Further technical effects include hearing aid and monitoring system that include a hearing aid and coupled remote resource, such as a smartphone or smartwatch, that can monitor a user's responses to verbal communication directed at the user to determine if the user is suffering from hearing loss, dementia, and/or to identify mechanical and/or electrical issues related to the hearing aid.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed:

1. A computer implemented method to monitor a user's hearing and comprehension, the method comprising:
receiving, by an audio capture device, a first audio input;
receiving, by the audio capture device, a second audio input, wherein the first audio input includes a voice of the user and wherein the second audio input includes a voice of a person having a conversation with the user;
converting the first and second audio inputs into respective first and second audio signals;
transcribing the first and second audio signals into respective first and second transcriptions;
analyzing the first and second transcriptions to determine if a content of the second transcription semantically matches a content of the first transcription, wherein the analysis includes an identification of cognitive breaks in the conversation between the user and the person and the identification of concepts within the content of the transcriptions to determine possible degradation of hearing of the user.

2. The computer implemented method of claim 1 wherein a determination that the content of the second transcription is not related to the content of the first transcription will indicate possible degradation of hearing of the user.

3. The computer implemented method of claim 1 further comprising recording the analysis to track a hearing and comprehension ability of the user.

4. The computer implemented method of claim 3 further comprising transmitting the recorded analysis to a healthcare provider.

5. The computer implemented method of claim 1 wherein the audio capture device is a hearing aid.

6. The computer implemented method of claim 1 further comprising transmitting the first and second audio signals to a remote resource wherein the remote resource is a smartwatch or a smart phone.

7. The computer implemented method of claim 1 further comprising generating a notification indicating a loss of hearing or lack of understanding.

8. The computer implemented method of claim 1 further comprising generating a user profile based on language usage by the user, pitch, tone, and cadence, wherein the user profile includes indicia to identify a voice of the user.

9. A system to monitor a user's hearing and comprehension comprising:
an audio capture device;
a remote resource in communication with the audio capture device, the remote resource including a memory having computer readable instructions and a processor configured to execute the computer readable instructions, the computer readable instructions comprising:
receiving, by the audio capture device, a first audio input;
receiving, by the audio capture device, a second audio input, wherein the first audio input includes a voice of the user and wherein the second audio input includes a voice of a person having a conversation with the user;
converting the first and second audio inputs into respective first and second audio signals;
transmitting said first and second audio signals to the remote resource;
transcribing the first and second audio signals into respective first and second transcriptions;
analyzing the first and second transcriptions to determine if a content of the second transcription semantically matches a content of the first transcription, wherein the analysis includes an identification of cognitive breaks in the conversation between the user and the person and the identification of concepts within the content of the transcriptions to determine possible degradation of hearing of the user.

10. The system of claim 9 wherein a determination that the content of the second transcription is not related to the content of the first transcription will indicate possible degradation of hearing of the user.

11. The system of claim 9 wherein the computer readable instructions further comprise recording the analysis to track a hearing and comprehension ability of the user.

12. The system of claim 9 wherein the computer readable instructions further comprise transmitting the recorded analysis to a healthcare provider.

13. The system of claim 9 wherein the audio capture device is a hearing aid and the remote resource is a smartwatch or a smart phone.

14. The system of claim 9 wherein the computer readable instructions further comprise generating a notification indicating a loss of hearing or lack of understanding.

15. The system of claim 9 wherein the computer readable instructions further comprise generating a user profile based on language usage by the user, pitch, tone, and cadence, wherein the user profile includes indicia to identify a voice of the user.

16. The system of claim 9 wherein the computer readable instructions further comprise displaying at least the first transcription on a display of the remote device.

17. A computer program product to monitor a user's hearing and comprehension, the computer program product comprising a remote resource having computer readable storage medium having program instructions embodied therewith and in communication with an audio capture device configured to capture a first audio input and a second audio input, wherein the first audio input includes a voice of the user and wherein the second audio input includes a voice of a person having a conversation with the user, and transmit a related first audio signal and a second audio signal to the remote resource, the program instructions executable by a processor to cause the processor to:
transcribe the first and second audio signals into respective first and second transcriptions;
analyze the first and second transcriptions to determine if a content of the second transcription semantically matches a content of the first transcription, wherein the analysis includes an identification of cognitive breaks in the conversation between the user and the person and the identification of concepts within the content of the transcriptions to determine possible degradation of hearing of the user.

18. The computer program product of claim 17, the processor further caused to record the analysis in the computer readable storage medium to track a hearing and comprehension ability of the user and to transmit the recorded analysis to a healthcare provider.

19. The computer program product of claim 17, the processor further caused to generate a notification indicating a loss of hearing or lack of understanding.

20. The computer program product of claim 17, the processor further caused to generate a user profile based on language usage by the user, pitch, tone, and cadence, wherein the user profile includes indicia to identify a voice of the user.

* * * * *